United States Patent [19]

Kupper

[11] Patent Number: 4,820,881
[45] Date of Patent: Apr. 11, 1989

[54] DECOLORIZATION

[75] Inventor: Robert J. Kupper, Mt. Airy, Md.

[73] Assignee: W. R. Grace & Co.-Conn., New York, N.Y.

[21] Appl. No.: 198,021

[22] Filed: May 24, 1988

[51] Int. Cl.$^4$ ...................... C07C 79/04; C07C 79/10; C01B 11/04
[52] U.S. Cl. ............................... 568/947; 252/187.27; 252/187.28; 210/917; 423/473; 423/474; 568/948; 568/943; 568/939; 568/927; 568/924
[58] Field of Search ...................... 252/187.27, 187.28; 568/924, 927, 939, 940, 943, 947, 948; 210/917; 423/473, 474

[56] References Cited

U.S. PATENT DOCUMENTS

| | | |
|---|---|---|
| 3,944,383 | 3/1976 | Davis . |
| 3,956,165 | 5/1976 | Hansen et al. .................. 252/187.28 |
| *4,210,609 | 7/1980 | Summers et al. . . |
| 4,605,508 | 8/1986 | Dodge et al. ........................ 423/474 |

FOREIGN PATENT DOCUMENTS 38-9725  3/1960  Japan .
45-1408  5/1970  Japan .

Primary Examiner—John F. Terapane
Assistant Examiner—Susan Wolffe
Attorney, Agent, or Firm—Howard J. Troffkin

[57] ABSTRACT

A process to decolorize and stabilize nitro compounds by contacting the nitro compound with an alkaline earth metal hypochlorite particulate material.

14 Claims, No Drawings

DECOLORIZATION

BACKGROUND OF THE INVENTION

The present invention is directed to a method of decolorizing and stabilizing nitro compounds, in particular nitroparaffins, to provide a high grade product.

Nitroparaffins are commercially produced by vapor phase nitration of paraffin feed stock. The composition of the product stream depends on the paraffin feed utilized but is, in general, a mixture of nitromethane, nitroethane, as well as 1- and 2-nitropropanes. Vapor phase nitration of saturated hydrocarbons higher than methane are taught in U.S. Pat. Nos. 3,780,115; 3,869,253; 4,260,838; and 4,313,010 as well as an improved process of U.S. Pat. No. 4,458,094 in which a small amount of an oxygenated hydrocarbon is introduced as part of the feed stock. Production of specific nitro compounds has been achieved by contacting at elevated temperature and pressure, under homogeneous gas phase conditions a specific substrate compound selected from olefin, ketone, alcohol, or carboxylic acids with nitrogen dioxide alone or in the presence of oxygen and/or water as taught in U.S. Pat. Nos. 4,517,392; 4,517,393; 4,517,394; 4,524,226 and copending U.S. Ser. No. 649,765 filed Sept. 12, 1984.

The nitroparaffin products have been known to suffer from color development while being stored even over short periods of time. The identity of the colorizing materials nor the mechanism of their formation has ever been established. The removal of the colorants has been difficult to accomplish especially in view of the high activity of the nitro product, per se. The lack of ability to remove the color from nitro compounds has hindered their commercial usage even though they are known to be excellent solvents in a variety of applications.

U.S. Pat. No. 4,210,609 and Japanese No. 45-14048 teach a method of removing colorants from nitro paraffins by passing the nitro compound through a bed of activated alumina ('609) or distilling the nitro compound over a bed of activated alumina, aluminum fluoride or sodium silicofluoride. These processes have been known to exhibit spontaneous decomposition of the substrate causing catastrophic results.

It is highly desired to provide a method of treating nitro compounds to remove the colorants therefrom and to impart storage stability with respect to future color development.

SUMMARY OF THE INVENTION

The present invention provides a simple and safe means of decolorizing nitro compounds, such as nitroparaffins, and to provide stability against color development during storage.

The present method requires contacting off-colored nitro compound with solid alkaline earth metal hypochlorite salt at low to moderate temperatures. The resultant product is of high color purity and exhibits stability to further discoloration.

DETAILED DESCRIPTION

The nitro compounds which can be effectively treated by the present method include nitroalkanes, nitrocycloalkanes and nitroalkyl aromatic compounds which are liquid under the treatment conditions of the present method. Normally, the compounds have from one to ten carbon atoms and include nitromethane, nitroethane, 1-nitropropane, 2-nitropropane, 1-nitrobutane, 3-nitropentane as well as other nitroparaffin ($C_1$–$C_{10}$) compounds; the nitrocycloalkanes, such as nitrocyclohexane, nitrocyclopentane and the like; and the nitroalkyl aromatics, such as alpha-nitrotoluene, beta-nitroethyl benzene and the like. These nitro compounds are known to develop coloration after short periods of storage. The present process has been found to be particularly useful to the highly desired commercial class of nitro compounds, the nitroparaffins.

Generally, commercial grades of the subject nitro compounds, that is material that has been subjected to usual rectification procedures, such as fractional distillation, will develop color beyond that of the "water-white" grade which is desired and, in some cases, required. A color grade scale has been developed by the American Public Health Association (APHA) and this scale is used herein and in the appended claims. The "water-white" color is normally associated with an APHA value of 20. Nitro compounds normally develop coloration of 50 APHA and higher and nitroparaffins have coloration of 60 APHA or more with values of 90 APHA and greater being associated with lower nitro paraffins.

The metal hypochlorite salt can be formed from any alkaline earth metal, such as calcium, magnesium and the like with calcium being preferred. The hypochlorite salt must be insoluble with respect to the nitro compound it is being contacted. The hypochlorite salt can be in any form. Normally granular or particulate material is desired. Although the exact mesh or particle size of the material is not critical, the size should be chosen to permit the most effective contact between the nitro compound and the hypochlorite salt material. This will depend on the particular mode of contact, the scale of the operation, and the means of separating the treated nitro compound from the salt. The particular size can be readily adjusted by the artisan. The hypochlorite salt will normally have a particle size of from about 200 mesh to $\frac{1}{4}$ inch or greater.

The hypochlorite salt and the liquid nitro compound are contacted by any means. The liquid nitro compound can be passed through a bed packed with particulate hypochlorite salt by any conventional procedure such as by pumping, by gravity feed, by trickle bed and the like. Alternately, the nitro compound and the hypochlorite salt can be contacted by forming a slurry of the materials. The nitro compound can be separated by appropriate means such as by distillation, filtration or the like or by a combination thereof. For example, a nitro compound can be passed through a trickle bed of calcium hypochlorite to produce a water-white material which may be then subjected to distillation to provide a ultra high purity material.

The nitro compound should be contacted with the hypochlorite salt for a sufficient time to provide the desired degree of decolorization. The time will depend upon the color value of the initial material. When the nitro compound is passed through a bed of hypochlorite salt, the space velocity will normally be from 0.1 to 100 or more bed volumes per hour with from 10 to 20 being preferred. In the case of a slurry treatment, the weight ratio of salt to nitro compound will normally be from about 1:1 to 1:100 with from about 1:4 to 1:50 being preferred although amounts lesser or greater than this may be applicable.

The present process should be carried out at low to moderate temperatures such as between about 0° to 50°

C. Normally, the pressure of the system is ambient although it is sometimes desirable, especially with nitro compounds having high vapor pressure at the operating temperature, to have small elevations of pressure to maintain the nitro compound in the liquid state.

The resultant nitro compound has been found to have high clarity and a color of 20 APHA or lower with color values of 10 APHA and lower being common. The treated nitro compound is color stable, that is it did not develop coloration on subsequent storage. The nitro compound is not chemically modified by the hypochlorite salt and is thus a high purity product.

The following examples are given for purposes of illustration only and are not meant to be a limitation on the subject invention. All parts and percentages are by weight unless otherwise indicated.

EXAMPLE 1

25.6 parts of orange colored 2-nitropropane (APHA color of 70) was placed in a glass vessel and mixed with 4 parts of dry calcium hypochlorite. The mixture was stirred for one hour at 25° C. and atmospheric pressure and then passed through a filter (0.2 micron). The resultant liquid 2-nitropropane was clear and had a color value of 0-5 AHPA. The nitropropane was analyzed by gas-liquid phase chromatography and by gas-liquid mass spectral analysis and showed no formation of chlorinated nitroparaffin material or residue hypochlorite salt present. The product was stored for 24 weeks and again analyzed to show that its color had not changed.

EXAMPLE 2

The procedure of Example 1 was repeated to decolorize 1-nitropropane having a APHA color of 60-70. The nitropropane was stirred for 2 hours with calcium hypochloride. The resultant product had a APHA color of 5-10, did not form a chlorinated product and retained its clear coloration after storage for 24 weeks.

EXAMPLE 3

The procedure of Example 1 was repeated to decolorize 2-nitropropane having a APHA color of greater than 100. The resultant material had a APHA color of 0-5, did not form a chlorinated product and retained its clear coloration after storage for 24 weeks.

What is claimed:

1. A process for decolorizing liquid nitro compounds containing color bodies comprising contacting the nitrocompound with an alkaline earth metal hypochlorite salt.

2. The process of claim 1 wherein the nitro compound is a nitroparaffin.

3. The process of claim 1 wherein the hypochlorite salt is granular having a particle size of from about 200 mesh to about ¼ inch diameter.

4. The process of claim 2 wherein the hypochlorite salt is granular having a particle size of from about 200 mesh to about ¼ inch diameter.

5. The process of claim 1 wherein the nitro compound and hypochlorite salt are contacted by forming a slurry of said compound and salt and the decolorized nitro compound is recovered by filtration, distillation or a combination thereof.

6. The process of claim 2 wherein the nitro compound and hypochlorite salt are contacted by forming a slurry of said compound and salt and the decolorized nitro compound is recovered by filtration, distillation or a combination thereof.

7. The process of claim 3 wherein the nitro compound and hypochlorite salt are contacted by forming a slurry of said compound and salt and the decolorized nitro compound is recovered by filtration, distillation or a combination thereof.

8. The process of claim 1 wherein the nitro compound is passed through a bed of granular hypochlorite salt having a particle size of from about 200 mesh to ¼ inch diameter.

9. The process of claim 2 wherein the nitro compound is passed through a bed of granular hypochlorite salt having a particle size of from about 200 mesh to ¼ inch diameter.

10. A process for decolorizing a liquid nitro compound selected from nitroparaffins or nitrocycloalkanes having one to ten carbon atoms by contacting the nitro compound with calcium hypochlorite and subsequently separating the decolorized nitro compound.

11. The process of claim 10 wherein the nitro compound is nitroparaffins selected from nitromethane, nitroethane, 1-nitropropane, 2-nitropropane and mixtures thereof.

12. The process of claim 11 wherein the separated nitro compound is fractionally distilled.

13. The process of claim 11 wherein the contact is made by slurry of the nitro compound with the hypochlorite.

14. The process of claim 11 wherein the nitro compound is passed through a bed of hypochlorite.

* * * * *